United States Patent
Kudo et al.

(10) Patent No.: US 11,948,349 B2
(45) Date of Patent: Apr. 2, 2024

(54) LEARNING METHOD, LEARNING DEVICE, GENERATIVE MODEL, AND PROGRAM

(71) Applicant: FUJIFILM Corporation, Tokyo (JP)

(72) Inventors: Akira Kudo, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 65 days.

(21) Appl. No.: 17/400,150

(22) Filed: Aug. 12, 2021

(65) Prior Publication Data
US 2021/0374483 A1 Dec. 2, 2021

Related U.S. Application Data

(63) Continuation of application No. PCT/JP2020/007382, filed on Feb. 25, 2020.

(30) Foreign Application Priority Data

Feb. 28, 2019 (JP) ................. 2019-036373

(51) Int. Cl.
*G06K 9/62* (2022.01)
*G06F 18/21* (2023.01)
(Continued)

(52) U.S. Cl.
CPC .......... *G06V 10/82* (2022.01); *G06F 18/2148* (2023.01); *G06F 18/2185* (2023.01);
(Continued)

(58) Field of Classification Search
CPC ............... G06K 9/6264; G06K 9/6257; G06V 30/2504; G06V 2201/03; A61B 6/032
See application file for complete search history.

(56) References Cited

U.S. PATENT DOCUMENTS

2010/0067772 A1 3/2010 Kitamura
2017/0347974 A1* 12/2017 Izumo .................... A61B 6/488
(Continued)

FOREIGN PATENT DOCUMENTS

| EP | 3447721 | 2/2019 |
| JP | 2008167950 | 7/2008 |
| JP | 2018192264 | 12/2018 |

OTHER PUBLICATIONS

You et al, "CT Super-resolution GAN Constrained by the Identical, Residual, and Cycle Learning Ensemble (GAN-Circle)," 2018, asarXiv:1808.04256v3 (17 Pages) (Year: 2018).*
(Continued)

*Primary Examiner* — David F Dunphy
(74) *Attorney, Agent, or Firm* — JCIPRNET

(57) ABSTRACT

Provided are a learning method, a learning device, a generative model, and a program that generate an image including high resolution information without adjusting a parameter and largely correcting a network architecture even in a case in which there is a variation of the parts of an image to be input. Only a first image is input to a generator of a generative adversarial network that generates a virtual second image having a relatively high resolution by using the first image having a relatively low resolution, and a second image for learning or the virtual second image and part information of the second image for learning or the virtual second image are input to a discriminator that identifies the second image for learning and the virtual second image.

12 Claims, 17 Drawing Sheets

(51) Int. Cl.
*G06F 18/214* (2023.01)
*G06K 9/68* (2006.01)
*G06V 10/10* (2022.01)
*G06V 10/12* (2022.01)
*G06V 10/82* (2022.01)
*G06V 30/24* (2022.01)
*A61B 6/03* (2006.01)

(52) U.S. Cl.
CPC .............. *G06V 10/12* (2022.01); *G06V 10/16* (2022.01); *G06V 30/2504* (2022.01); *A61B 6/032* (2013.01); *G06V 2201/03* (2022.01)

(56) References Cited

U.S. PATENT DOCUMENTS

2018/0260957 A1  9/2018  Yang et al.
2018/0336677 A1  11/2018  Sloan et al.
2018/0341836 A1  11/2018  Lim et al.

OTHER PUBLICATIONS

Ian J. Goodfellow et al., "Generative Adversarial Nets," arXiv:1406.2661, Jun. 2014, pp. 1-9.
Phillip Isola et al., "Image-to-Image Translation with Conditional Adversarial Networks," CVPR2016, Nov. 2016, pp. 1-17.
Mehdi Mirza et al., "Conditional Generative Adversarial Nets," arXiv:1411.1784, Nov. 2014, pp. 1-7.
Akira Kudo et al., "Virtual Thin Slice: 3D Conditional GAN-based Super-resolution for CT Slice Interval," arXiv:1908.11506, Sep. 2019, pp. 1-10.
"International Search Report (Form PCT/ISA/210) of PCT/JP2020/007382," dated Apr. 14, 2020, with English translation thereof, pp. 1-5.
"Written Opinion of the International Searching Authority (Form PCT/ISA/237)" of PCT/JP2020/007382, dated Apr. 14, 2020, with English translation thereof, pp. 1-7.
Morteza Mardani et al., "Deep Generative Adversarial Networks for Compressed Sensing (GANCS) Automates MRI," arXiv:1706.00051v1, May 2017, pp. 1-12.
Rewa Sood et al., "An Application of Generative Adversarial Networks for Super Resolution Medical Imaging," 2018 17th IEEE International Conference on Machine Learning and Applications, Dec. 2018, pp. 326-331.
Qing Lyu et al., "Super-resolution MRI through Deep Learning," arXiv:1810.06776, Oct. 2018, pp. 1-7.
Kun Zeng et al., "Simultaneous single- and multi-contrast super-resolution for brain MRI images based on a convolutional neural network," Computers in Biology and Medicine, vol. 99, Aug. 2018, pp. 133-141.
Morteza Mardani et al., "Deep Generative Adversarial Neural Networks for Compressive Sensing MRI," IEEE Transactions on Medical Imaging, vol. 38, Jan. 2019, pp. 167-179.
"Search Report of Europe Counterpart Application", dated Mar. 25, 2022, p. 1-p. 8.
"Office Action of Japan Counterpart Application" with English translation thereof, dated Apr. 26, 2022, p. 1-p. 4.

* cited by examiner

FIG. 11
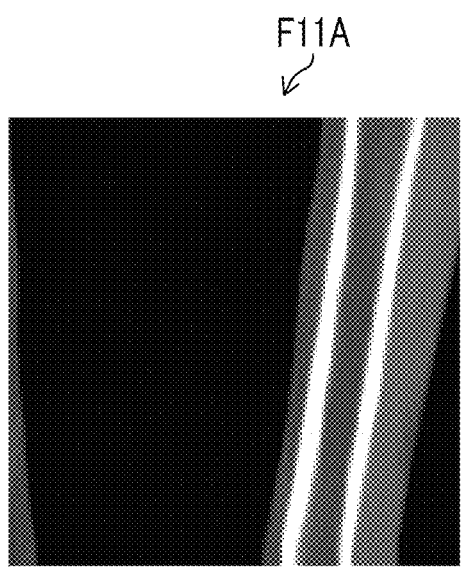
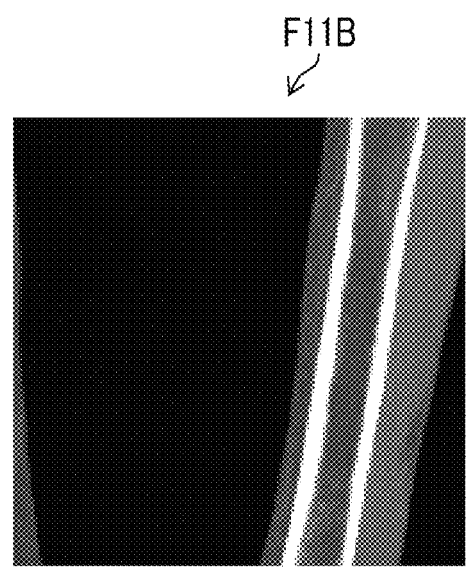

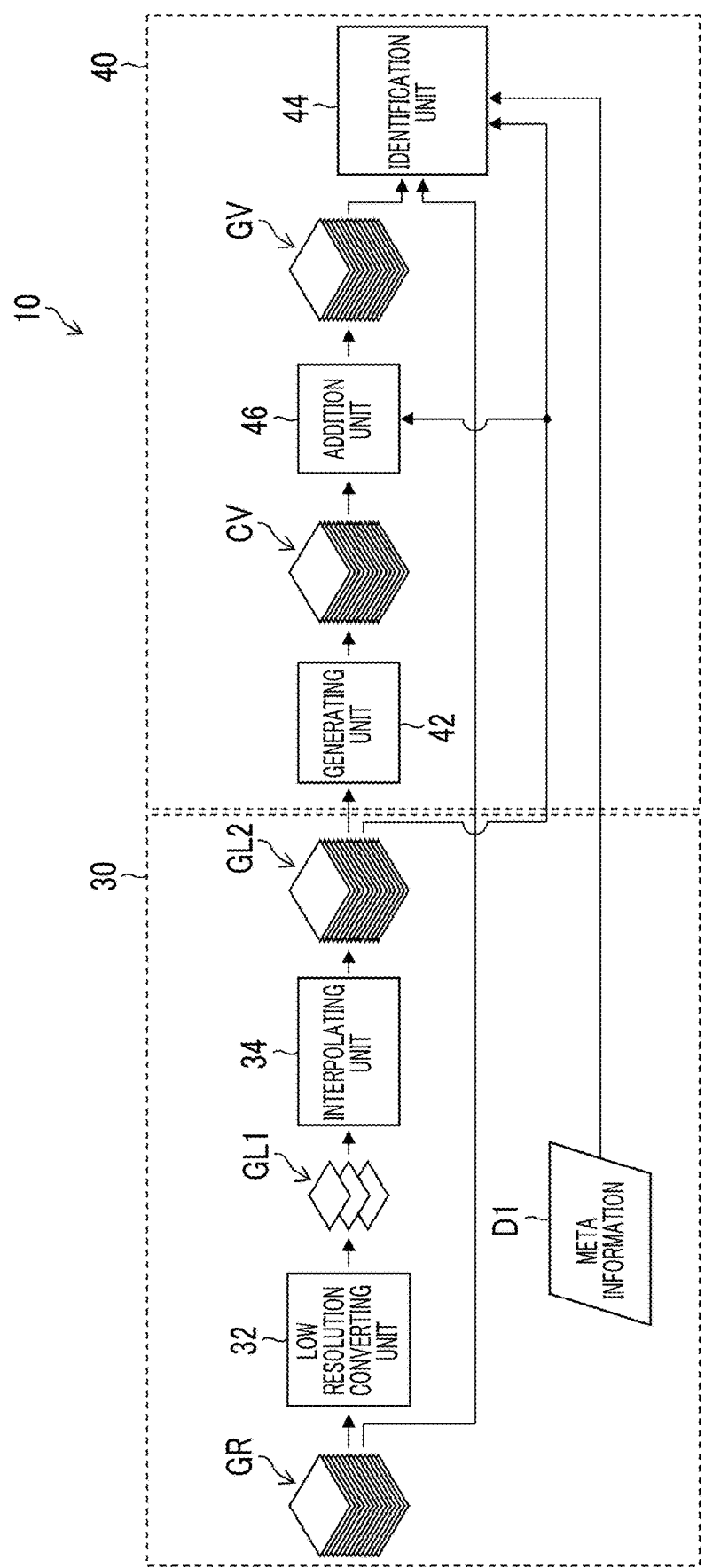

LEARNING METHOD, LEARNING DEVICE, GENERATIVE MODEL, AND PROGRAM

CROSS-REFERENCE TO RELATED APPLICATIONS

The present application is a Continuation of PCT International Application No. PCT/JP2020/007382 filed on Feb. 25, 2020 claiming priority under 35 U.S.C § 119(a) to Japanese Patent Application No. 2019-036373 filed on Feb. 28, 2019. Each of the above applications is hereby expressly incorporated by reference, in its entirety, into the present application.

BACKGROUND OF THE INVENTION

1. Field of the Invention

The present invention relates to a learning method, a learning device, a generative model, and a program, and particularly to a technique for generating a high resolution image.

2. Description of the Related Art

There is known a generative adversarial network (GAN) that alternately learns a "generator" that produces data and a "discriminator" that identifies the data. Ian J. Goodfellow, Jean Pouget-Abadie, Mehdi Mirza, Bing Xu, David Warde-Farley, Sherjil Ozair, Aaron Courville, Yoshua Bengio "Generative Adversarial Nets", arXiv:1406.2661 discloses a study of the GAN. With the GAN, it is possible to learn a generative model that generates highly accurate data in line with the characteristics of learning data.

In addition, a technique for applying the GAN is researched. Phillip Isola, Jun-Yan Zhu, Tinghui Zhou, Alexei A. Efros "Image-to-Image Translation with Conditional Adversarial Networks", CVPR2016 discloses a method for learning a pair of an input image and an output image by using the GAN. With the method disclosed in Phillip Isola, Jun-Yan Zhu, Tinghui Zhou, Alexei A. Efros "Image-to-Image Translation with Conditional Adversarial Networks", CVPR2016, it is possible to learn the generative model with less burden of parameter adjustment.

Image generation of the GAN has a problem that learning is difficult in a case in which there is a variation of input data. For example, in a medical image, in a case in which the part in the image to be input and the slice conditions are various, the features of the generated image are averaged. Even in a case in which various input data are handled as in Phillip Isola, Jun-Yan Zhu, Tinghui Zhou, Alexei A. Efros "Image-to-Image Translation with Conditional Adversarial Networks", CVPR2016, the characteristics of the learning data are averaged.

On the other hand, Mehdi Mirza, Simon Osindero "Conditional Generative Adversarial Nets", arXiv: 1411.1784 discloses a method of using data category information for learning the GAN. With the method disclosed in Mehdi Mirza, Simon Osindero "Conditional Generative Adversarial Nets", arXiv: 1411.1784, the generative model can be adjusted based on the category information.

SUMMARY OF THE INVENTION

However, in the GAN configuration disclosed in Mehdi Mirza, Simon Osindero "Conditional Generative Adversarial Nets", arXiv: 1411.1784, since it is necessary to input the category information to the generator, there is a problem that the network architecture needs to be largely corrected and the generator interface becomes complicated.

In addition, the GAN is strongly influenced by a part of the learning data, and has a problem called mode collapse, in which the generated images are limited and variation thereof cannot be handled.

The present invention has been made in view of such circumstances, and is to provide a learning method, a learning device, a generative model, and a program that performs various learning to generate an image including high resolution information without adjusting a parameter and largely correcting the network architecture.

One aspect of a learning method for achieving the above object is a learning method of a generative model that estimates, from a first image including low resolution information having a relatively low resolution, a second image including high resolution information having a relatively high resolution, the method comprising a generator input step of inputting only the first image to a generator of a generative adversarial network including the generator which is a generative model that generates a virtual second image by using the first image and a discriminator that identifies a second image for learning and the virtual second image, a first discriminator input step of inputting the second image for learning and part information of the second image for learning to the discriminator, and a second discriminator input step of inputting the virtual second image and part information of the virtual second image to the discriminator.

According to the aspect, only the first image is input to the generator of the generative adversarial network, the part information is input to the discriminator, and learning is performed for each condition by adding the part information to be input, so that various learning is can be performed to generate an image including high resolution information without adjusting a parameter and largely correcting the network architecture.

The first image including the low resolution information having a relatively low resolution has, for example, a low resolution. The second image including the high resolution information having a relatively high resolution is, for example, a high resolution image. Further, the second image may be a high-frequency component image including the high resolution information having a relatively high resolution.

It is preferable that the part information include a head, a chest, an abdomen, and a leg part of a human body. This makes it possible to generate the image including the high resolution information from the images of various parts of the human body, which includes the low resolution information.

It is preferable that the first image be a three-dimensional tomographic image, and the resolution be a resolution in a slice thickness direction. This makes it possible to generate the three-dimensional tomographic image including the high resolution information in the slice thickness direction.

It is preferable that in the first discriminator input step and the second discriminator input step, slice information of the first image be input to the discriminator. This makes it possible to generate the high resolution image even in a case in which there is a variation of the slice information of the input image.

It is preferable that the slice information be a slice interval. This makes it possible to generate the high resolution image even in a case in which there is a variation of the slice interval of the input image.

It is preferable that the slice information be a slice thickness. This makes it possible to generate the high resolution image even in a case in which there is a variation of the slice thickness of the input image.

It is preferable that in the first discriminator input step and the second discriminator input step, the first image be input to the discriminator. Therefore, the discriminator can appropriately identify the second image for learning and the virtual second image.

It is preferable that the learning method further comprise a first image generation step of generating the first image from the second image for learning, in which in the generator input step, only the generated first image is input to the generator. This makes it possible to appropriately acquire the image including the low resolution information for input to the generator.

One aspect of a program that causes a computer to execute for achieving the above object is a program that causes a computer to execute the learning method described above.

One aspect of a generative model for achieving the above object is a generative model that estimates, from a first image including low resolution information having a relatively low resolution, a second image including high resolution information having a relatively high resolution, the generative model being learned by the learning method described above.

One aspect of a learning device for achieving the above object is a learning device of a generative model that estimates, from a first image including low resolution information having a relatively low resolution, a second image including high resolution information having a relatively high resolution, the device comprising a generative adversarial network that includes a generator which is a generative model that generates a virtual second image by using the first image and a discriminator that identifies a second image for learning and the virtual second image, a generator input unit that inputs only the first image to the generator, a first discriminator input unit that inputs the second image for learning and part information of the second image for learning to the discriminator, and a second discriminator input unit that inputs the virtual second image and part information of the virtual second image to the discriminator.

According to the aspect, only the first image is input to the generator of the generative adversarial network, the part information is input to the discriminator, and learning is performed for each condition by adding the part information to be input, so that various learning is can be performed to generate an image including high resolution information without adjusting a parameter and largely correcting the network architecture.

According to the present invention, it is possible to perform various learning to generate the image including the high resolution information without adjusting the parameter and largely correcting the network architecture.

BRIEF DESCRIPTION OF THE DRAWINGS

FIG. 11 is a diagram showing an image of a leg part.

FIG. 17 is a functional block diagram showing learning processing of the medical image learning device 10 according to a fourth embodiment.

DESCRIPTION OF THE PREFERRED EMBODIMENTS

Preferred embodiments of the present invention will be described below in detail with reference to the accompanying drawings.

<Hardware Configuration of Medical Image Learning Device>

Figure 1:
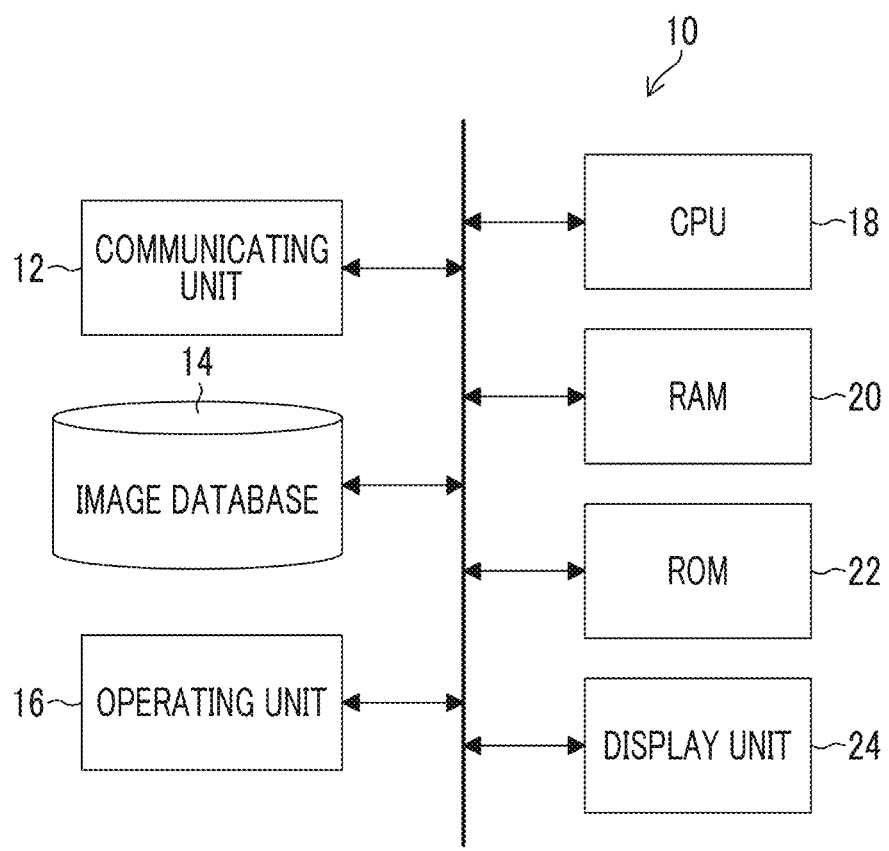
FIG. 1 is a block diagram showing an example of a hardware configuration of a medical image learning device according to an embodiment of the present invention.

FIG. 1 is a block diagram showing an example of a hardware configuration of a medical image learning device according to an embodiment of the present invention. The medical image learning device 10 is configured by a personal computer or a workstation. The medical image learning device 10 is mainly configured by a communicating unit 12, an image database 14, an operating unit 16, a central processing unit (CPU) 18, a random access memory (RAM) 20, a read only memory (ROM) 22, and a display unit 24.

The communicating unit 12 is an interface that performs communication processing with an external device by wire or wirelessly and exchanges information with the external device.

The image database 14 is a large-capacity storage device that stores a computed tomography (CT) reconstructed image (CT image) captured by a medical X-ray CT device. The image database 14 may be provided in the outside of the medical image learning device 10. In this case, the medical image learning device 10 acquires the CT image from the image database 14 via the communicating unit 12.

The operating unit 16 is an input interface that receives various operation inputs with respect to the medical image learning device 10. As the operating unit 16, a keyboard or mouse (not shown) that is wired or wirelessly connected to the computer is used.

The CPU 18 reads out various programs stored in the ROM 22, a hard disk apparatus (not shown), and the like, and executes various processing. The RAM 20 is used as a work region of the CPU 18. Further, the RAM 20 is used as a storage unit that temporarily stores the read program and various data. The medical image learning device 10 may comprise a graphics processing unit (GPU).

The display unit 24 is an output interface on which information necessary for the medical image learning device 10 is displayed. As the display unit 24, a liquid crystal monitor (not shown) or the like that can be connected to the computer is used.

In the medical image learning device 10, the CPU 18 reads out a medical image learning program stored in the ROM 22 or the hard disk apparatus or the like in response to an instruction input from the operating unit 16, and executes the medical image learning program. As a result, a learning method of the medical image described below is implemented, and learning of a generative model that estimates, from a first image including low resolution information having a relatively low resolution in the CT image, a second image including high resolution information having a relatively high resolution is performed.

The medical image learning program that causes the computer to execute the learning method of the medical image may be provided by being stored in a computer-readable non-temporary recording medium.

<Part Information and Slice Information of CT Image>

The CT image stored in the image database 14 is the medical image obtained by imaging a human body (subject), and is a three-dimensional tomographic image including a plurality of slice images (axial cross-sectional images). Here, each slice image is an image parallel to the X direction and the Y direction which are orthogonal to each other. The Z direction orthogonal to the X direction and the Y direction is the body axis direction of the subject, and is also called to a slice thickness direction.

The CT image stored in the image database 14 is the image for each part of the human body. The CT image may be the image captured for each part, or may be the image obtained by cutting out, for each part, the image obtained by capturing a whole body. Each CT image stored in the image database 14 is stored in association with part information and slice information.

The part information is information indicating the part captured in the CT image. The part information includes a head, a chest, an abdomen, and a leg part. The part information may include a lumbar region.

In addition, the slice information includes at least one of a slice interval or a slice thickness of the CT image. The slice interval is a difference in position between slice images adjacent to each other in the Z direction, and is also referred to as slice spacing. Further, the slice thickness is the width (thickness) of one slice image in the Z direction, and is also referred to as slice thickness.

Figure 2:
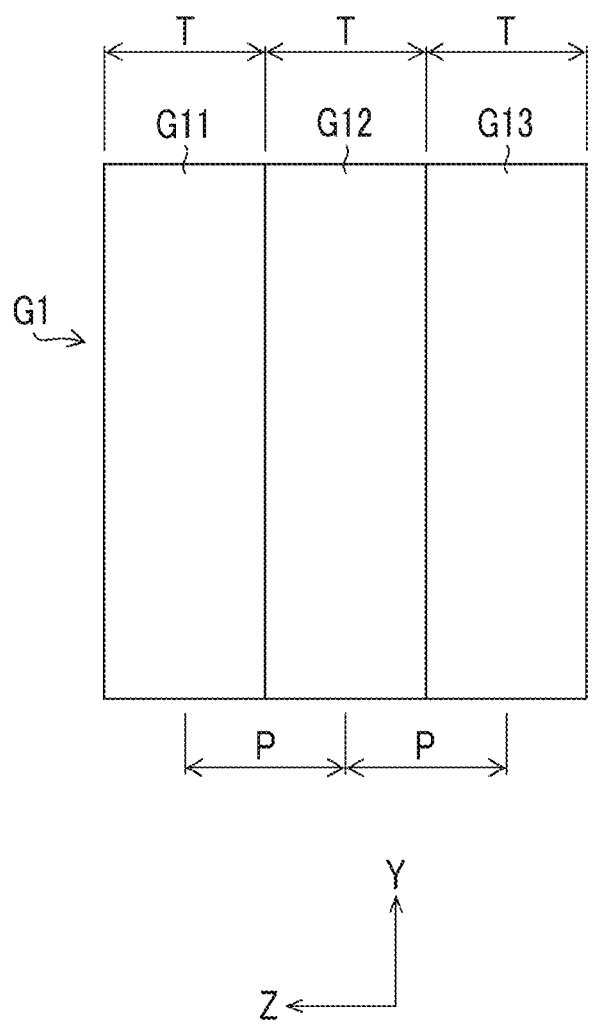
FIG. 2 is a diagram for explaining a slice interval and a slice thickness of a CT image.

FIGS. 2 to 5 are diagrams for explaining examples of the slice interval and the slice thickness of the CT image. A CT image G1 shown in FIG. 2 is configured to include slice images G11, G12, and G13. In the CT image G1, a slice interval P is 4 mm and a slice thickness T is 4 mm. That is, the difference in the position in the Z direction between the slice image G11 and the slice image G12 and the difference in the position in the Z direction between the slice image G12 and the slice image G13 are respectively 4 mm. The thicknesses of the slice images G11, G12, and G13 in the Z direction are respectively 4 mm. In the CT image G1, the slice interval P and the slice thickness T are equal, and thus the slice image G11 and the slice image G12, and the slice image G12 and the slice image G13 are in contact with each other in the Z direction.

Figure 3:
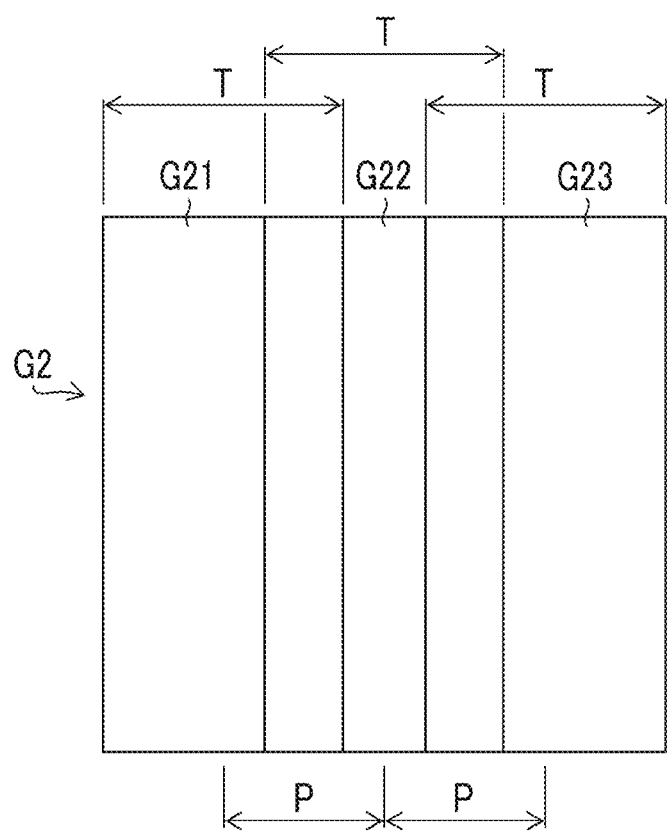
FIG. 3 is a diagram for explaining the slice interval and the slice thickness of the CT image.

A CT image G2 shown in FIG. 3 is configured to include slice images G21, G22, and G23. In the CT image G2, the slice interval P is 4 mm and the slice thickness T is 6 mm. The CT image G2 has the slice thickness T larger than the slice interval P, and thus the slice image G21 and the slice image G22, and the slice image G22 and the slice image G23 overlap each other in the Z direction.

Figure 4:
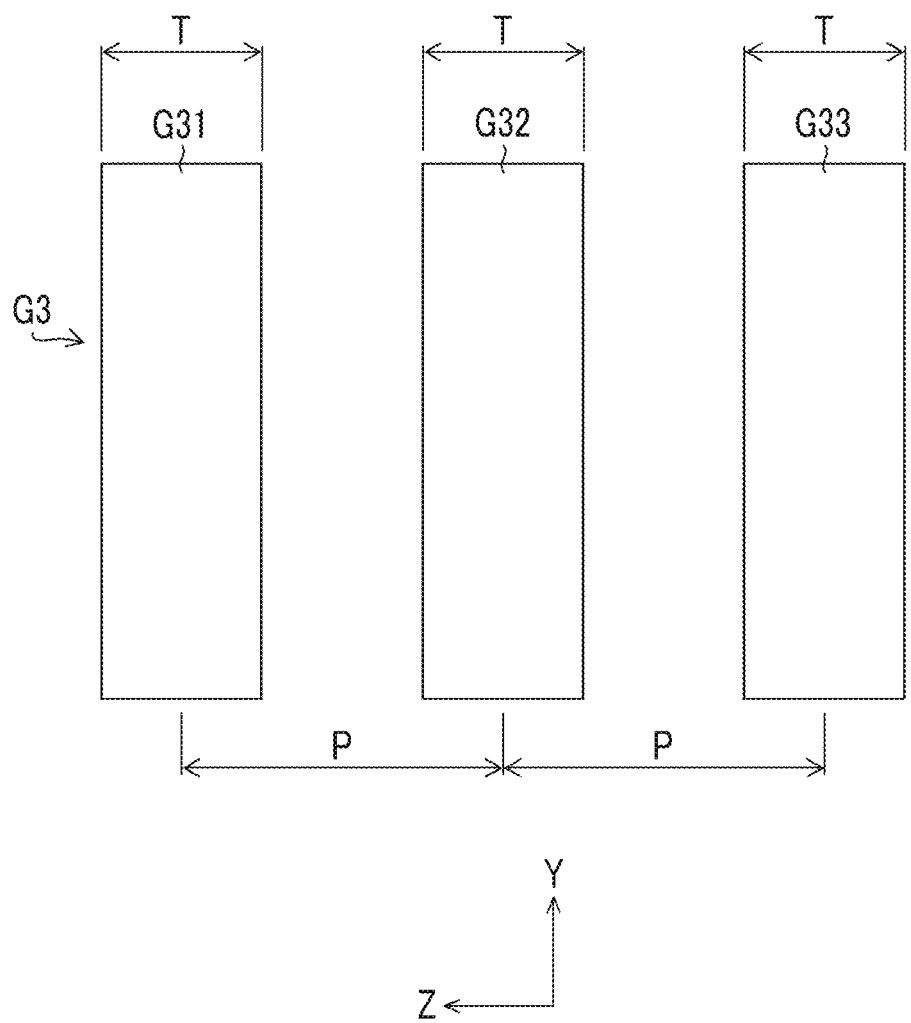
FIG. 4 is a diagram for explaining the slice interval and the slice thickness of the CT image.

A CT image G3 shown in FIG. 4 is configured to include slice images G31, G32, and G33. In the CT image G3, the slice interval P is 8 mm and the slice thickness T is 4 mm. The CT image G3 has the slice interval P larger than the slice thickness T, and thus the slice image G31 and the slice image G32, and the slice image G32 and the slice image G33 are separated from each other in the Z direction.

Figure 5:
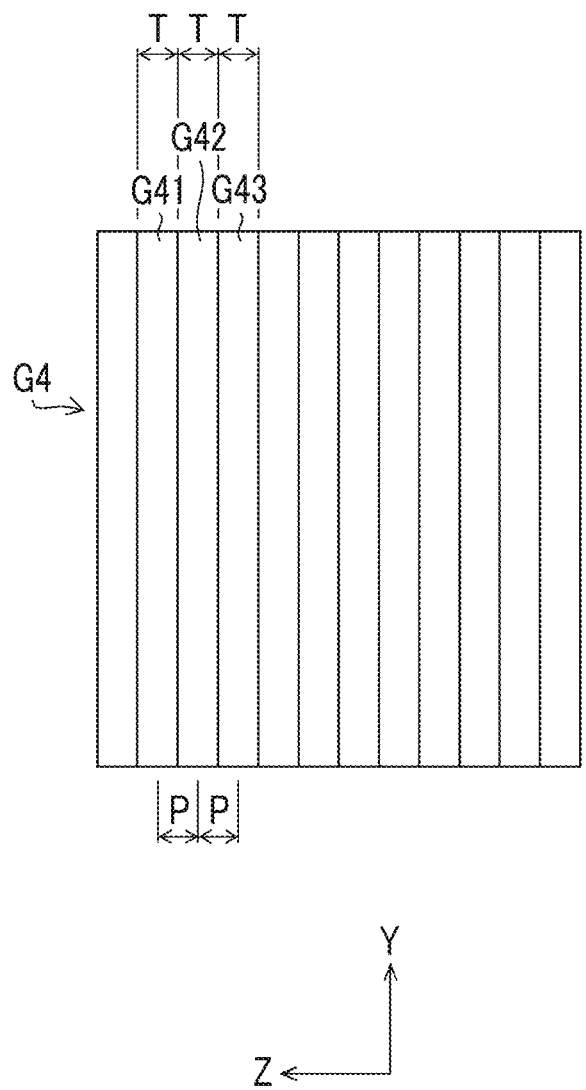
FIG. 5 is a diagram for explaining the slice interval and the slice thickness of the CT image.

A CT image G4 shown in FIG. 5 is configured to include slice images G41, G42, and G43. In the CT image G4, the slice interval P is 1 mm and the slice thickness T is 1 mm. The CT image G4 has a larger amount of information than the CT images G1, G2, and G3 in the Z direction. That is, the CT image G4 has a relatively high resolution than the CT images G1, G2, and G3 in the Z direction.

The slice interval and slice thickness of the CT image are set under various conditions depending on the facility at which the CT device is used or the preference of a doctor. It is preferable that the CT image have high resolution for diagnosis, but there is a problem that the amount of exposure to the subject is increased. In addition, the CT image has a large amount of data, so that the CT image may be stored at a lower resolution in order to reduce the capacity.

The medical image learning device 10 performs learning of the generative model that estimates a high resolution CT image having the slice interval of 1 mm and the slice thickness of 1 mm shown in FIG. 5 from a low resolution CT image having the slice intervals and the slice thicknesses under various conditions as shown in FIGS. 2 to 4.

First Embodiment

[Functional Block of Medical Image Learning Device]

Figure 6:
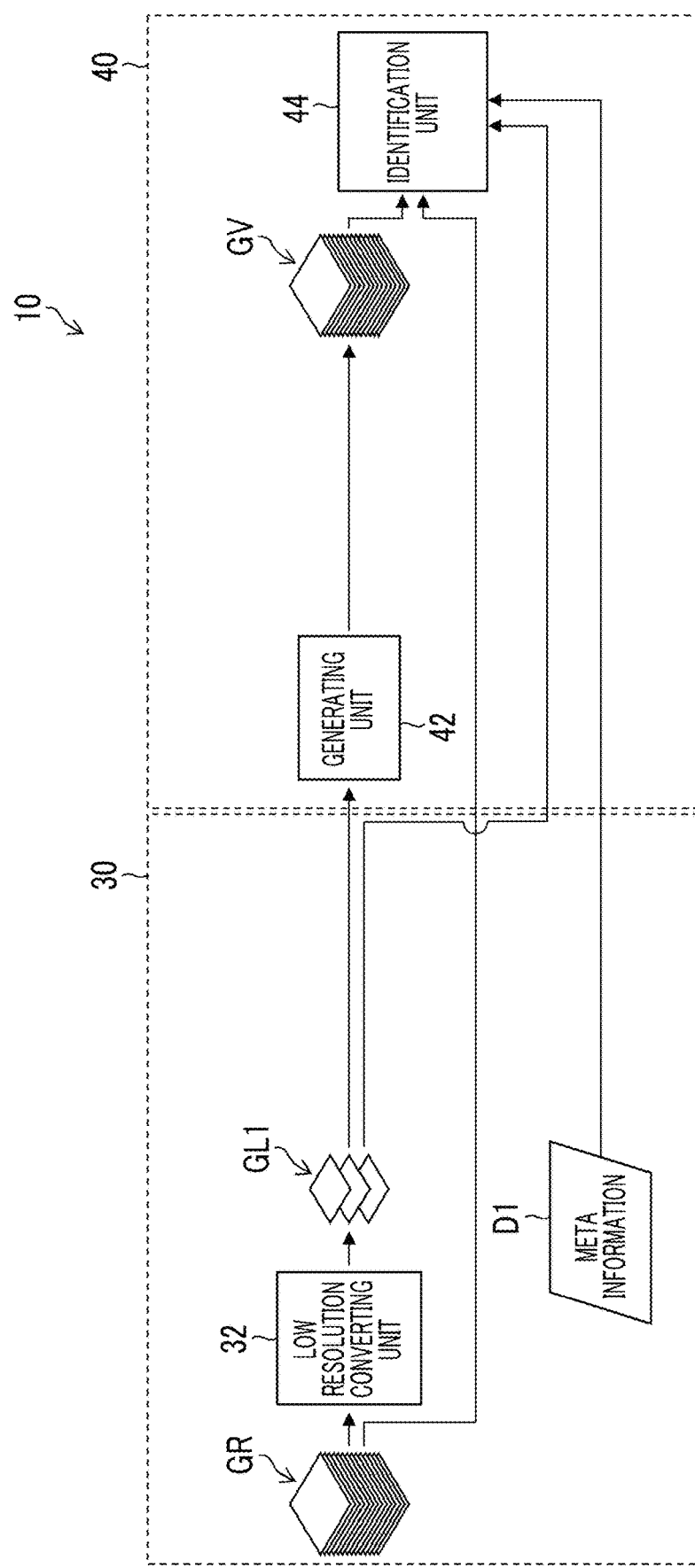
FIG. 6 is a functional block diagram showing learning processing of a medical image learning device 10 according to a first embodiment.

FIG. 6 is a functional block diagram showing learning processing of the medical image learning device 10 according to the first embodiment. The medical image learning device 10 comprises an input unit 30 and a learning unit 40. The functions of the input unit 30 and the learning unit 40 are realized by each unit of the medical image learning device 10 shown in FIG. 1.

The input unit 30 generates data (learning data) necessary for learning of the learning unit 40, and inputs the generated learning data to the learning unit 40. The input unit 30 acquires an original high resolution image GR (real thin image) captured by the CT device (not shown) and the part information and the slice information associated with the original high resolution image GR from the image database 14 (see FIG. 1).

The input unit 30 comprises a low resolution converting unit 32. The low resolution converting unit 32 artificially generates various low resolution images GL1 (thick images) based on data of the input original high resolution image GR. The low resolution converting unit 32 performs posture conversion on, for example, the slice image equalized to 1 mm, randomly cuts out a region, and virtually generates the low resolution image GL1 having the slice interval and the slice thickness of 4 mm or 8 mm.

Further, the low resolution converting unit 32 may generate the low resolution image GL1 by down-sampling processing that simply thins out and reduces the input original high resolution image GR.

The input unit 30 inputs the original high resolution image GR and the low resolution image GL1 to the learning unit 40. Further, the input unit 30 inputs meta information D1 (condition) to the learning unit 40.

The meta information D1 includes the part information and the slice information. The part information is information common to the original high resolution image GR, and the low resolution image GL1. The slice information of the low resolution image GL1 is used as the slice information. The slice information of the low resolution image GL1 can be acquired from the slice information associated with the original high resolution image GR and the contents of the low resolution conversion processing performed by the low resolution converting unit 32.

The learning unit 40 is based on a structure obtained by extending the architecture disclosed in Mehdi Mirza, Simon Osindero "Conditional Generative Adversarial Nets", arXiv: 1411.1784 from two-dimensional data to three-dimensional data. The learning unit 40 constructs a generative adversarial network (GAN). The GAN comprises a "generator" that produces the data and a "discriminator" that identifies the data. The learning unit 40 comprises a generating unit 42 corresponding to the "generator" and an identification unit 44 corresponding to the "discriminator". The learning unit 40 learns the generating unit 42 by repeating adversarial learning using the identification unit 44 based on the data input from the input unit 30. The generating unit 42 corresponds to the generative model that estimates, from the first image including the low resolution information having a relatively low resolution, the second image including the high resolution information having a relatively high resolution.

Only the low resolution image GL1 (example of first image) is input to the generating unit 42 from the input unit 30 (example of generator input unit). The generating unit 42 generates a virtual high resolution image GV having the same resolution as the original high resolution image GR from the input low resolution image GL1.

In the identification unit 44, a pair of the original high resolution image GR (example of second image for learning) and the low resolution image GL1 which are input from the input unit 30 or a pair of the virtual high resolution image GV (example of virtual second image) and the low resolution image GL1 which are input from the generating unit 42 (example of discriminator input unit) is input.

Further, in the identification unit 44, a new channel is secured. The meta information D1 is input to the new channel of the identification unit 44. The identification unit 44 uses the low resolution image GL1 and the meta information D1 to identify whether the input high resolution image is the original high resolution image GR or the virtual high resolution image GV. The identification result of the identification unit 44 is input to the generating unit 42.

Figure 7:
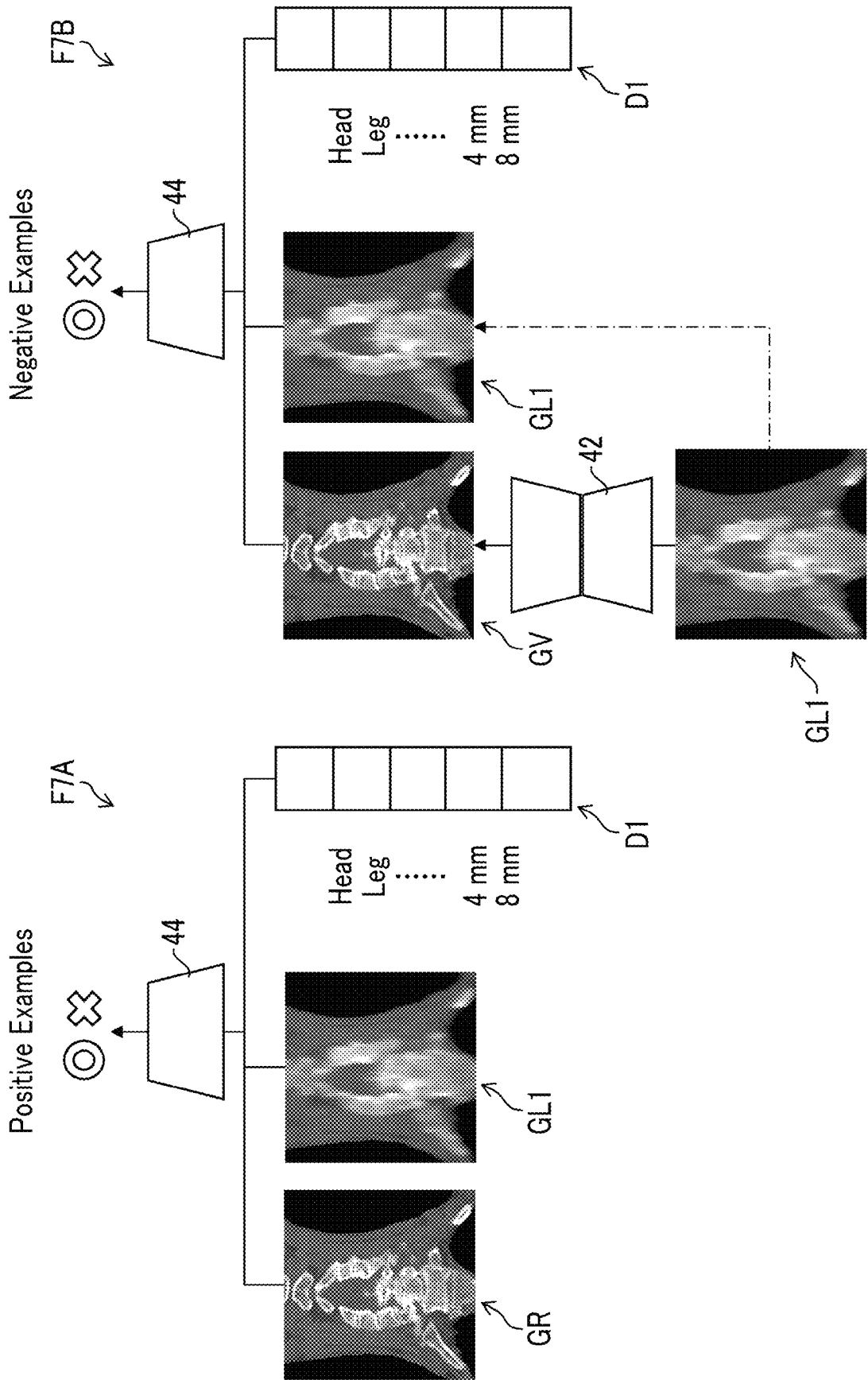
FIG. 7 is a diagram for explaining identification by an identification unit 44 at the time of learning.

FIG. 7 is a diagram for explaining identification by the identification unit 44 at the time of learning. In the case of F7A of FIG. 7, the low resolution image GL1, the meta information D1, and the original high resolution image GR are input to the identification unit 44. Therefore, in a case in which the identification unit 44 identifies the input high resolution image as the original high resolution image GR, it is correct, and in a case in which the identification unit 44 identifies the input high resolution image as a virtual high resolution image GV, it is incorrect.

On the other hand, in the case of F7B of FIG. 7, the low resolution image GL1, the meta information D1, and the virtual high resolution image GV generated by the generating unit 42 are input to the identification unit 44. Therefore, in a case in which the identification unit 44 identifies the input high resolution image as the original high resolution image GR, it is incorrect, and in a case in which the identification unit 44 identifies the input high resolution image as a virtual high resolution image GV, it is correct.

The identification unit 44 is learned to make the identification correct as to whether the input high resolution image is a real CT image captured by the CT device (not shown) or the virtual CT image generated by the generating unit 42. On the other hand, the generating unit 42 is learned to generate the virtual CT image resembling the real CT image captured by the CT device (not shown) and to make the identification of the identification unit 44 incorrect.

As the learning progresses, the generating unit 42 and the identification unit 44 increase each other's accuracy, and the generating unit 42 can generate the virtual high resolution image GV close to the real CT image, which is not identified by the identification unit 44. The generating unit 42 acquired by this learning is the generative model. The generating unit 42 and the identification unit 44 are learned by using, for example, a convolutional neural network.

[Learning Method of Medical Image]

Figure 8:
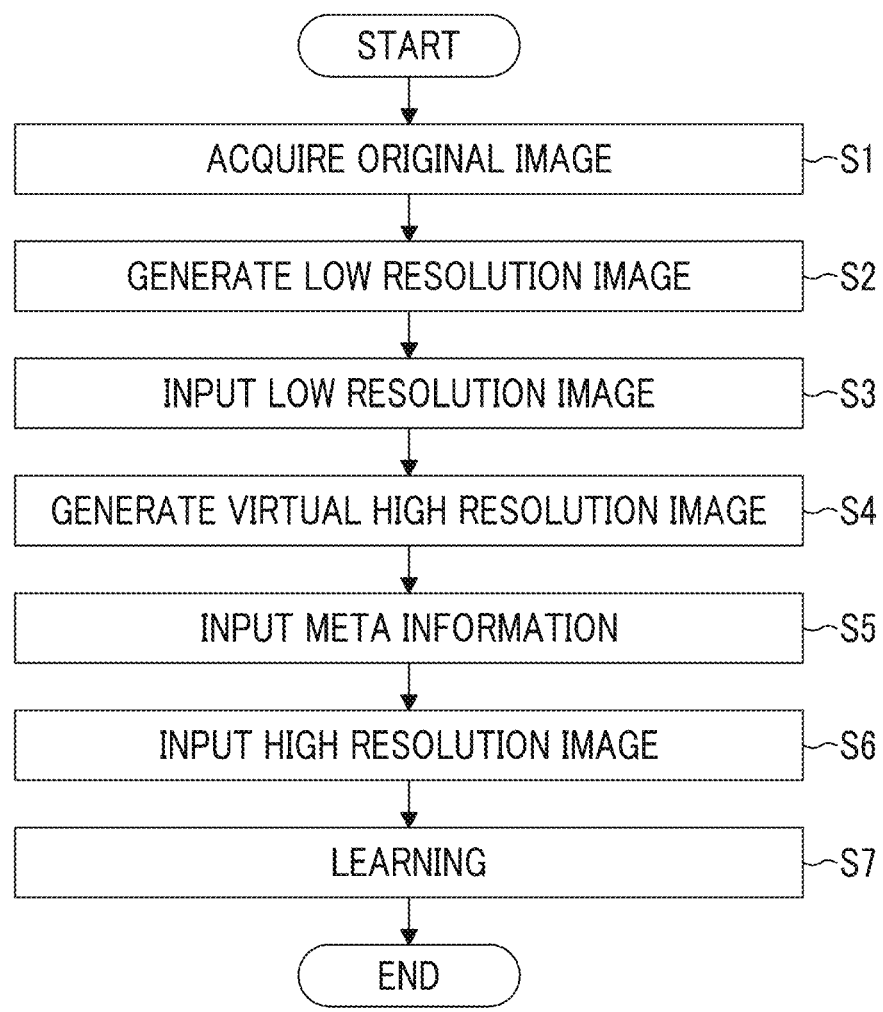
FIG. 8 is a flowchart showing an example of a learning method of a medical image of the medical image learning device 10.

FIG. 8 is a flowchart showing an example of the learning method of the medical image of the medical image learning device 10. As shown in FIG. 8, the learning method of the medical image comprises an original image acquiring step (step S1), a low resolution image generation step (step S2), a low resolution image input step (step S3), a virtual high resolution image generation step (step S4), a meta information input step (step S5), a high resolution image input step (step S6), and a learning step (step S7).

In step S1, the input unit 30 acquires the original high resolution image GR from the image database 14. Here, the original high resolution image GR equalized to the slice interval of 1 mm and the slice thickness of 1 mm is acquired.

In step S2 (example of first image generation step), the low resolution converting unit 32 generates the low resolution image GL1 from the input original high resolution image GR. Here, the low resolution converting unit 32 generates the low resolution image GL1 having the slice interval of 5 mm and the slice thickness of 1 mm. That is, the original high resolution image GR and the low resolution image GL1 have different resolution in the Z direction and have the same resolution in the X direction and the Y direction.

In step S3 (example of generator input step), the input unit 30 inputs the low resolution image GL1 generated in step S2 to the generating unit 42 of the learning unit 40. Only the low resolution image GL1 is input to the generating unit 42.

In step S4, the generating unit 42 generates the virtual high resolution image GV from the input low resolution image GL1. Here, the generating unit 42 generates the virtual high resolution image GV having the slice interval of 1 mm and the slice thickness of 1 mm.

In step S5 (example of first discriminator input step and example of second discriminator input step), the input unit 30 (example of first discriminator input unit and example of second discriminator input unit) inputs the meta information D1 to the identification unit 44 of the learning unit 40. The meta information D1 is the part information of the high resolution image to be input to the identification unit 44 in step S6 and the slice information of the low resolution image GL1. The part information of the original high resolution image GR and the virtual high resolution image GV is common to the part information of the low resolution image GL1. Therefore, the input unit 30 may input the part information of the low resolution image GL1 to the identification unit 44 as the part information of the meta information D1.

In step S6, the input unit 30 inputs the high resolution image to the identification unit 44 of the learning unit 40. The high resolution image is the original high resolution image GR or the virtual high resolution image GV. That is, the input unit 30 (example of first discriminator input unit) inputs the original high resolution image GR to the identification unit 44 (example of first discriminator input step) or the input unit 30 (example of second discriminator input unit) inputs the virtual high resolution image GV to the identification unit 44 (example of second discriminator input step). Further, the input unit 30 inputs the low resolution image GL1 to the identification unit 44 (example of first discriminator input unit and example of second discriminator input unit).

In step S7, the identification unit 44 uses the input low resolution image GL1 and the meta information D1 to identify whether the input high resolution image is the original high resolution image GR or the virtual high resolution image GV. The identification result of the identification unit 44 is input to the generating unit 42. As a result, the generating unit 42 and the identification unit 44 are learned.

By repeating the above learning method, the identification unit 44 is learned to be able to more suitably identify whether the input high resolution image is the original high resolution image GR or the virtual high resolution image GV. On the other hand, the generating unit 42 is learned to generate the virtual high resolution image GV close to the original high resolution image GR. As a result, the generating unit 42 can estimate the virtual high resolution image GV having a relatively high resolution from the low resolution image GL1 having a relatively low resolution.

Figure 9:
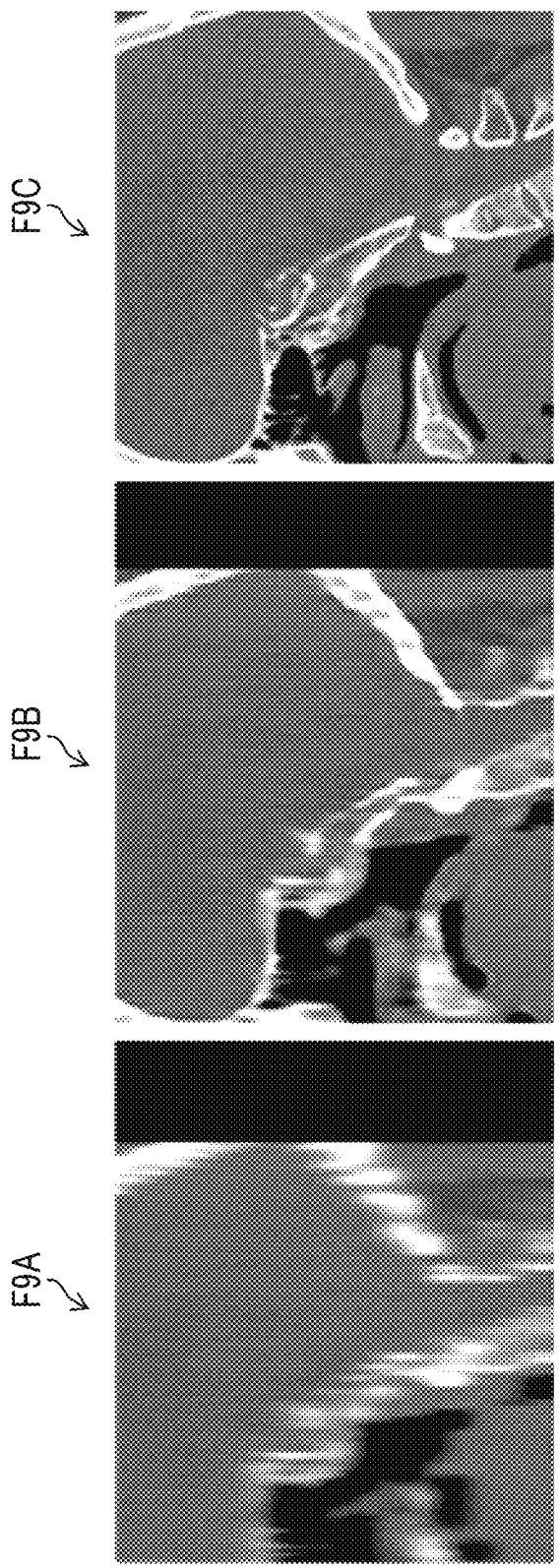
FIG. 9 is a diagram for explaining image generation in which an image of the whole body is learned without providing meta information D1.
Figure 10:
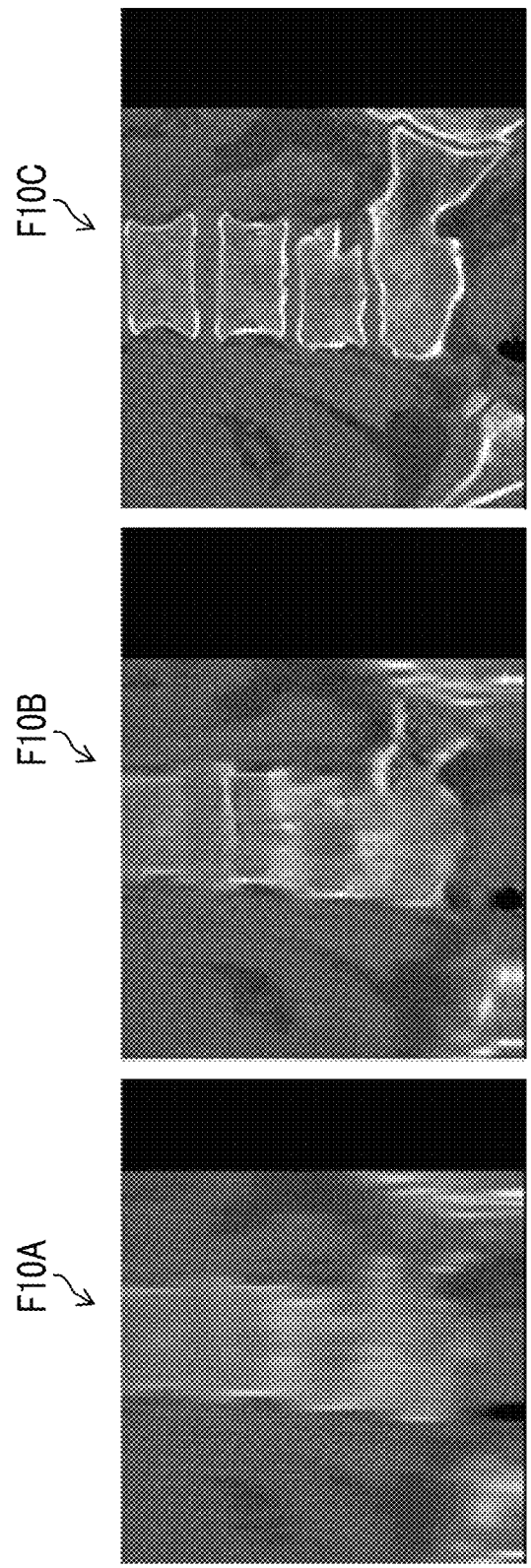
FIG. 10 is a diagram for explaining image generation in which the image of the whole body is learned without providing the meta information D1.

FIGS. 9 and 10 are diagrams for explaining image generation in the generating unit 42 that learns the image of the whole body without providing the meta information D1 to the identification unit 44. FIG. 9 shows sagittal cross-sectional images of the CT image of the head. F9A of FIG. 9 is the low resolution image input to the generating unit 42. F9B of FIG. 9 is the virtual high resolution image output from the generating unit 42. Further, F9C of FIG. 9 is the correct data (ground truth) of F9B, and is the original high resolution image which is the original data of F9A. FIG. 10 shows sagittal cross-sectional images of the CT image of the lumbar region. F10A, F10B, and F10C of FIG. 10 are the input low resolution image, the output virtual high resolution image, and the correct data, respectively.

Ideally, the generating unit 42 outputs the high resolution image close to the correct data in a case in which the low resolution image is input, regardless of the parts from the head to the leg part. However, as shown in FIGS. 9 and 10, in a case in which learning is performed without providing the meta information D1 to the identification unit 44, the virtual high resolution image generated by the generating unit 42 is affected by the learning of other parts, the feature thereof is averaged, and the image is obscured. The cause thereof is considered to be the variation of the input data.

FIG. 11 shows sagittal cross-sectional images of the CT image of the leg part. F11A of FIG. 11 is the low resolution image of the leg part. F11B of FIG. 11 is the high resolution image of the leg part. As shown in FIG. 11, the image of the leg part has a large amount of information in the background and the vertical direction, and the change between the low resolution image and the high resolution image is relatively small. Therefore, the generating unit 42 performs learning of "do almost nothing" with respect to generation of the high resolution image of the leg part. However, this learning has a problem that the learning of generation of the high resolution images of the head, the chest, and the abdomen is adversely affected.

Further, the identification unit 44 has a problem that the accuracy is not improved due to confusion due to the variation of the image parts.

As one method for such a problem, it is conceivable to learn and create identification (super resolution image output model) for each part. However, this method has new problems that a model is needed to be created for each part, the part of the data is needed to be determined at the time of inference, and the data across the parts is needed to be processed.

Figure 12:
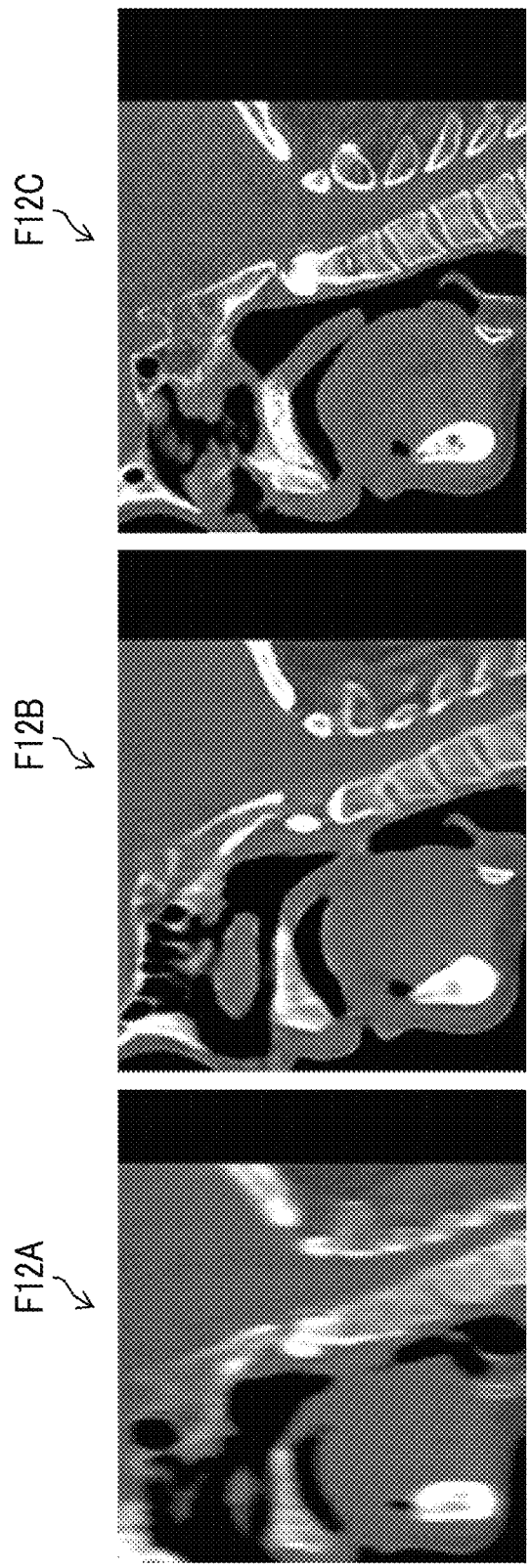
FIG. 12 is a diagram for explaining the effects of the embodiment.
Figure 13:
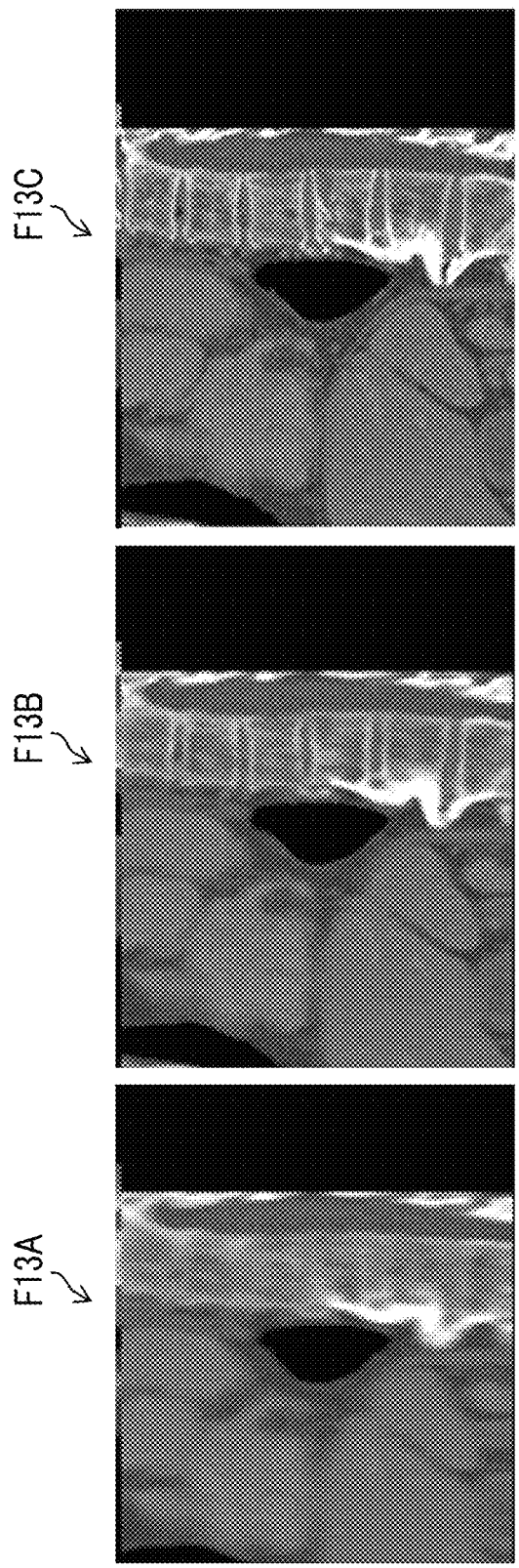
FIG. 13 is a diagram for explaining the effects of the embodiment.
Figure 14:
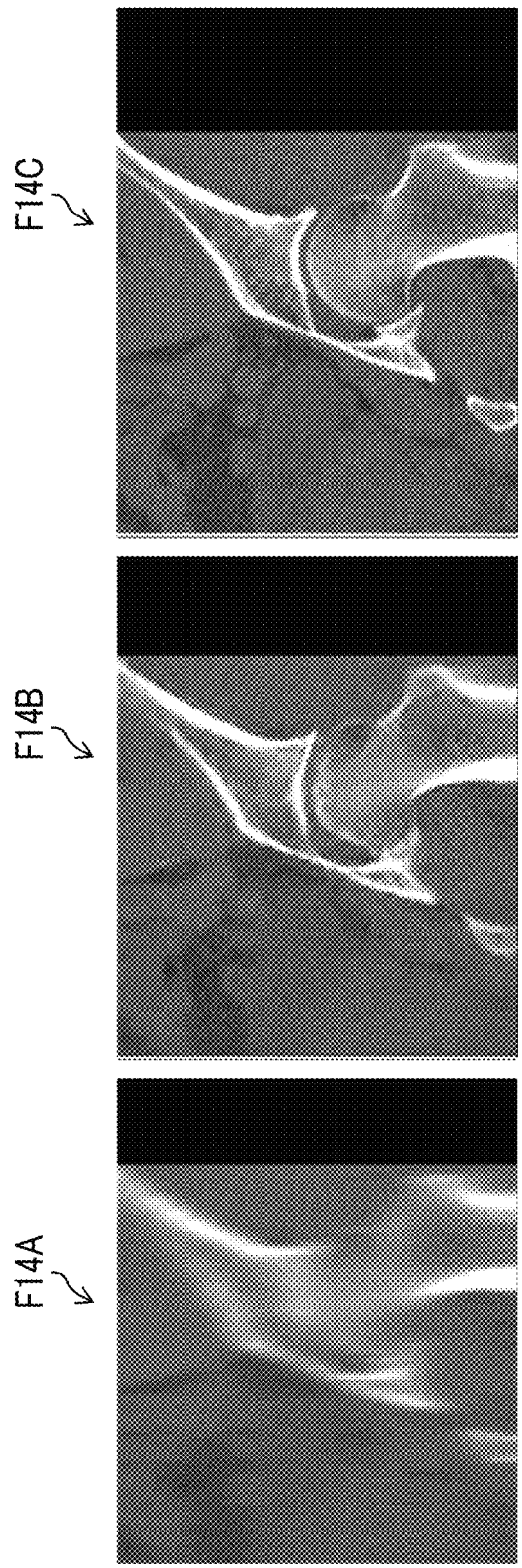
FIG. 14 is a diagram for explaining the effects of the embodiment.

FIGS. 12 to 14 are diagrams for explaining other effects of the present embodiment. FIG. 12 shows sagittal cross-sectional images of the CT image of the head. F12A of FIG. 12 is the low resolution image input to the generating unit 42, which is a learned generative model. F12B of FIG. 12 is the virtual high resolution image output from the generating unit 42. F12C of FIG. 12 is the correct data (ground truth) of F12B, and is the original high resolution image which is the original data of F12A. FIG. 13 shows sagittal cross-sectional images of the CT image of the abdomen. F13A, F13B, and F13C of FIG. 13 are the input low resolution image, the output virtual high resolution image, and the correct data, respectively. FIG. 14 shows sagittal cross-sectional images of the CT image of the lumbar region. F14A, F14B, and F14C of FIG. 14 are the images of the lumbar region, which are the input low resolution image, the output virtual high resolution image, and the correct data, respectively.

As shown in FIGS. 12 to 14, with the generating unit 42 learned according to the present embodiment, the meta information D1 is input to the identification unit 44 for learning, so that the image can be generated with high accuracy regardless of the part, the slice interval, or the like. This generating unit 42 can be applied to a virtual thin slice (VTS) device.

According to the present embodiment, it is not necessary to prepare the generative model for each part. In the present embodiment, only the low resolution image is input to the generating unit 42, and thus it is not necessary to largely correct the network architecture. In addition, the identification unit 44 can be learned by using the part information as the feature amount. As a result, the learned generative model does not need information about that the low resolution image to be input is an image of which part, and can generate the high resolution image regardless of which part of the image is input. Therefore, the assets of the past CT image can be effectively used. This generative model can generate the high resolution image even in a case in which the image across a plurality of parts is input.

Here, the input unit 30 inputs the part information and the slice information to the identification unit 44 as the meta information D1, but the meta information D1 need only include at least the part information. Further, the meta information D1 may include blur intensity information of the low resolution image. The blur intensity information may be classified into "high blur intensity", "low blur intensity", and the like.

Further, in the present embodiment, a pair of the original high resolution image GR and the low resolution image GL1 or a pair of the virtual high resolution image GV and the low resolution image GL1 which are input from the generating unit 42 is input to the identification unit 44, but the input of the low resolution image GL1 is not essential. That is, the original high resolution image GR or the virtual high resolution image GV need only be input to the identification unit 44.

Even in a case in which the low resolution image GL1 is not input to the identification unit 44, in a case in which the virtual high resolution image GV is input to the identification unit 44, the slice information of the low resolution image GL1 is used in the slice information of the meta information D1. This is to consider under what conditions the virtual high resolution image GV input to the identification unit 44 is generated based on the low resolution image GL1.

In a case in which the original high resolution image GR is input to the identification unit 44, the slice information has no meaning, so a random value is provided to the slice information for learning. As a result, the identification unit 44 can learn the identification for conditions such as "determination of real or fake of the high resolution image that has a possibility of fake, which is generated from the low resolution image having the slice interval of 4 mm", "determination of real or fake of the high resolution image that has a possibility of fake, which is generated from the low resolution image having the slice interval of 8 mm", or the like.

Second Embodiment

Figure 15:
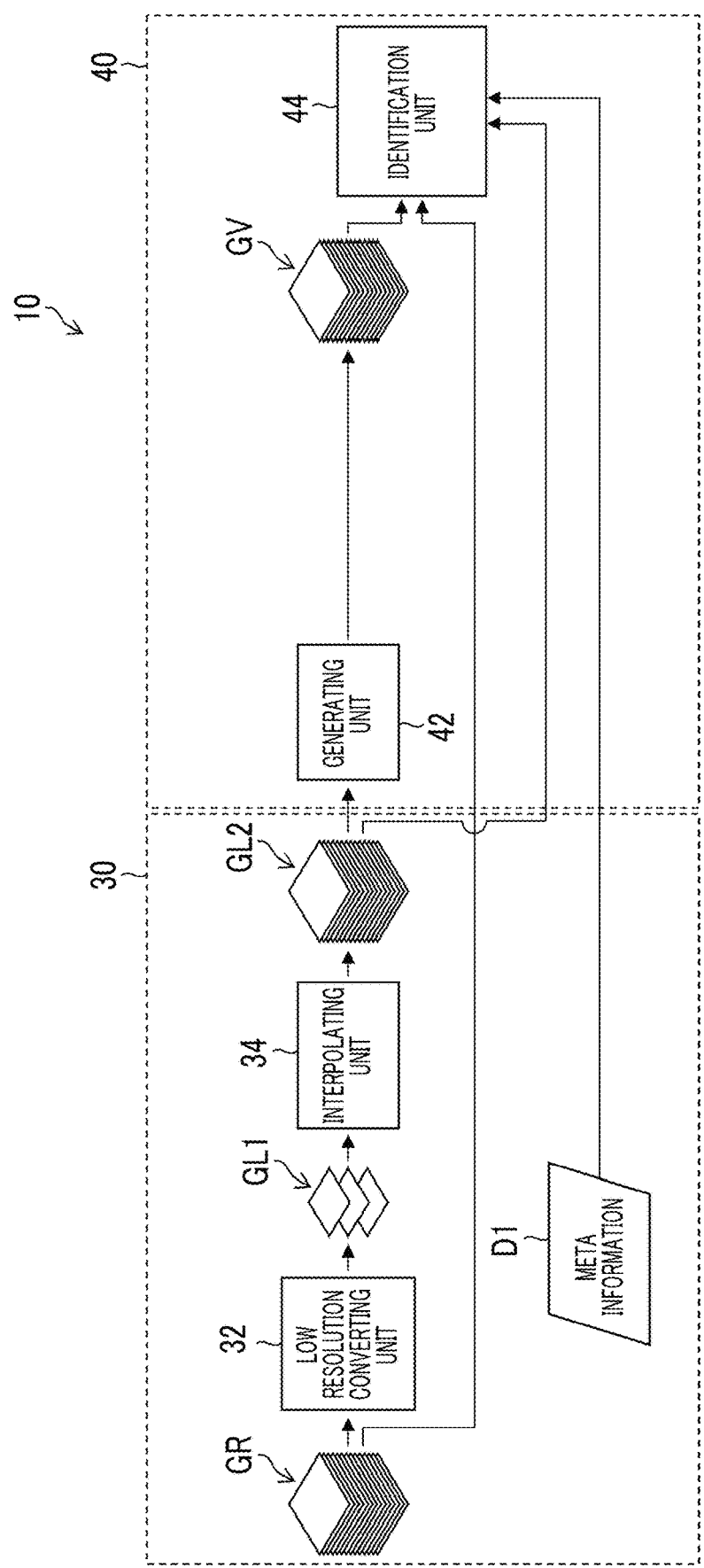
FIG. 15 is a functional block diagram showing learning processing of the medical image learning device 10 according to a second embodiment.

FIG. 15 is a functional block diagram showing the learning processing of the medical image learning device 10 according to a second embodiment. The portions common to those of the functional block diagram shown in FIG. 6 are designated by the same reference numerals, and detailed description thereof will be omitted.

The medical image learning device 10 comprises an interpolating unit 34 in the input unit 30. The interpolating unit 34 generates a low resolution image GL2 from the low resolution image GL1 generated by the low resolution converting unit 32. The interpolating unit 34 performs spline interpolation processing in the Z direction of the low resolution image GL1. Further, the interpolating unit 34 applies Gaussian filter processing to the low resolution image GL1 that is subjected to the spline interpolation processing. The image generated by the spline interpolation processing and the Gaussian filter processing is the low resolution image GL2.

For example, the low resolution image GL1 has the slice interval of 5 mm and the slice thickness of 1 mm, and the low resolution image GL2 generated by the interpolating unit 34 has the slice interval of 1 mm and the slice thickness of 1 mm. The slice interval and the slice thickness of the low resolution image GL2 are the same as the slice interval and the slice thickness of the original high resolution image GR, but the low resolution image GL2 is an image blurred in the Z direction as compared with the original high resolution image GR.

The low resolution image GL2 generated by the interpolating unit 34 is input to the generating unit 42 of the learning unit 40. That is, in the present embodiment, the generating unit 42 generates the virtual high resolution image GV from the low resolution image GL2. The slice interval and the slice thickness of the virtual high resolution image GV are the same as the slice interval and the slice thickness of the low resolution image GL2, but the virtual high resolution image GV is an image sharper in the Z direction as compared with the low resolution image GL2.

Further, the low resolution image GL2 generated by the interpolating unit 34 is input to the identification unit 44 in a pair with the high resolution image. The identification unit 44 uses the low resolution image GL2 and the meta information D1 to identify whether the input high resolution image is the original high resolution image GR or the virtual high resolution image GV. The low resolution image GL2 may not be input to the identification unit 44.

According to the present embodiment, the generating unit 42 can be learned to generate the high resolution image from the low resolution image GL2 that is subjected to low resolution conversion from the original high resolution image GR and further subjected to the spline interpolation processing. Therefore, by combining with the learning to generate the high resolution image from the low resolution image GL1, the generative model adapted to the low resolution image of various inputs can be obtained.

Third Embodiment

Figure 16:
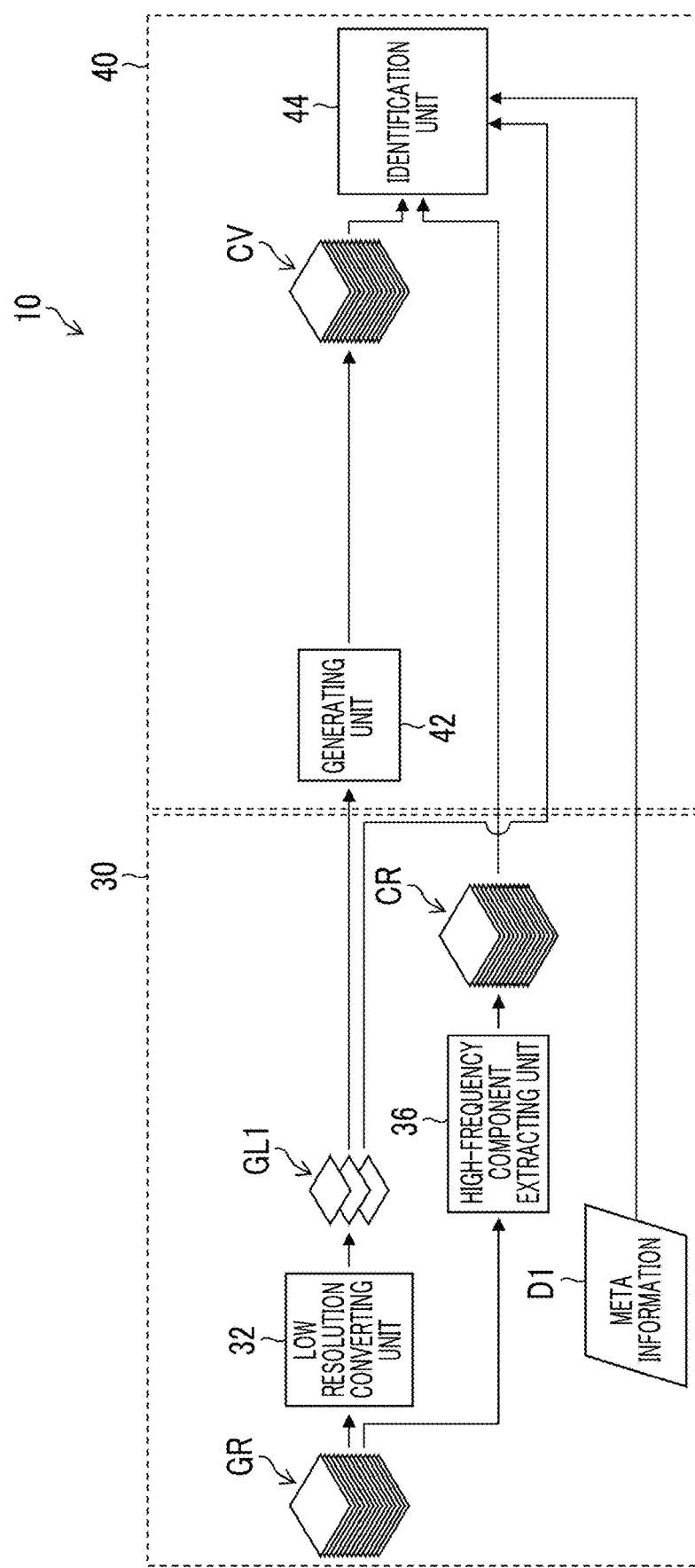
FIG. 16 is a functional block diagram showing learning processing of the medical image learning device 10 according to a third embodiment.

FIG. 16 is a functional block diagram showing the learning processing of the medical image learning device 10 according to a third embodiment. The portions common to those of the functional block diagram shown in FIG. 6 are designated by the same reference numerals, and detailed description thereof will be omitted. The medical image learning device 10 according to the present embodiment generates a high-frequency component image including the high resolution information having a relatively high resolution instead of the high resolution image and identifies the generated image.

The medical image learning device 10 comprises a high-frequency component extracting unit 36 in the input unit 30. The high-frequency component extracting unit 36 extracts high-frequency components from the original high resolution image GR and generates an original high-frequency component image CR (example of high-frequency component image for learning). Extraction of the high-frequency components is performed by using a high-pass filter. Similar to the original high resolution image GR, the original high-frequency component image CR has the slice interval of 1 mm and the slice thickness of 1 mm.

The original high-frequency component image CR generated by the high-frequency component extracting unit 36 is input to the identification unit 44 of the learning unit 40.

Further, the generating unit 42 of the learning unit 40 generates a virtual high-frequency component image CV having the same resolution as the original high-frequency component image CR from the low resolution image GL1 input from the low resolution converting unit 32 of the input unit 30. Here, the generating unit 42 generates the virtual high-frequency component image CV having the slice interval of 1 mm and the slice thickness of 1 mm.

In the identification unit 44, a pair of the original high-frequency component image CR (example of second image for learning) and the low resolution image GL1 which are input from the input unit 30 or a pair of the virtual high resolution image GV (example of virtual second image) and the low resolution image GL1 which are input from the generating unit 42 (example of discriminator input unit) is input.

The identification unit 44 uses the low resolution image GL1 and the meta information D1 input from the input unit 30 to identify whether the input high-frequency component image is the original high-frequency component image CR or the virtual high-frequency component image CV.

According to the present embodiment, the generating unit 42 can be learned to generate the high-frequency component image from the low resolution image GL1. The generating unit 42 can obtain the high resolution image by adding the high-frequency component image generated by the generating unit 42 and the low resolution image GL1 input from the generating unit 42.

Fourth Embodiment

FIG. 17 is a functional block diagram showing the learning processing of the medical image learning device 10 according to a fourth embodiment. The portions common to those of the functional block diagrams shown in FIGS. 15 and 16 are designated by the same reference numerals, and detailed description thereof will be omitted.

The low resolution converting unit 32 of the input unit 30 generates the low resolution image GL1 from the original high resolution image GR. The interpolating unit 34 generates the low resolution image GL2 from the low resolution image GL1.

The generating unit 42 of the learning unit 40 generates the virtual high-frequency component image CV having the same resolution as the original high resolution image GR from the low resolution image GL2 input from the interpolating unit 34 of the input unit 30.

The medical image learning device 10 comprises an addition unit 46 in the learning unit 40. The addition unit 46 adds the virtual high-frequency component image CV generated by the generating unit 42 and the low resolution image GL2 generated by the interpolating unit 34. As a result, the addition unit 46 generates the virtual high resolution image GV having the same resolution as the original high resolution image GR.

The pair of the original high resolution image GR and the low resolution image GL2 which are input from the input unit 30 or the pair of the virtual high resolution image GV and the low resolution image GL2 which are input from the addition unit 46 is input to the identification unit 44.

The identification unit 44 uses the low resolution image GL1 and the meta information D1 to identify whether the input high resolution image is the original high resolution image GR or the virtual high resolution image GV. The identification result of the identification unit 44 is input to the generating unit 42. As a result, the generating unit 42 and the identification unit 44 are learned.

According to the present embodiment, the generating unit 42 can be learned to generate the high-frequency component image from the low resolution image GL1. In addition, the identification unit 44 can be learned to identify the high resolution image.

Others

Here, an example in which the medical image learning device 10 is configured by one personal computer or workstation has been described, but the medical image learning device 10 may be configured by a plurality of the personal computers. For example, the input unit 30 and the learning unit 40 may be configured by different personal computers. With this configuration, the generation of the learning data and the learning of the generative model can be performed without being physically and temporally restricted by each other.

Here, the learning method of the super resolution generative model of the CT image has been described, but the learning method of the generative model according to the present embodiment can be applied to the three-dimensional tomographic image having the part information. For example, the learning method may be applied to a magnetic resonance (MR) image acquired by a magnetic resonance imaging (MM) device, a positron emission tomography (PET) image acquired by a PET device, an optical coherence tomography (OCT) image acquired by an OCT device, a three-dimensional ultrasound image acquired by a three-dimensional ultrasound imaging device, and the like.

Further, the learning method of the generative model according to the present embodiment can be applied to a two-dimensional image having the part information. For example, the learning method may be applied to an X-ray image. Further, the learning method is not applied only to the medical image, and can be applied to a normal camera image. In a case in which the learning method is applied to the two-dimensional image, sharpness (reconstruction function) information need only be used instead of the slice interval of the slice information. Further, instead of the slice thickness of the slice information, pixel spacing information, that is, pixel size information need only be used.

In the embodiments described so far, for example, the hardware structure of the processing unit that executes various processing of the medical image learning device 10 is the following various processors. The various processors include the CPU, which is a general-purpose processor that executes software (program) and functions as various processing units, a graphics processing unit (GPU) which is a processor specialized for image processing, a programmable logic device (PLD) that is a processor whose circuit configuration can be changed after manufacture such as a field programmable gate array (FPGA), and a dedicated electric circuit that is a processor which has a circuit configuration that is designed for exclusive use in order to execute specific processing such as an application specific integrated circuit (ASIC).

One processing unit may be configured by one of these various processors, or may be configured by two or more processors of the same type or different types (for example, a plurality of FPGAs, a combination of a CPU and a FPGA, or a combination of a CPU and a GPU). Alternatively, a plurality of processing units may be configured by one processor. As an example of configuring a plurality of processing units with one processor, first, as represented by a computer such as a server or a client, there is a form in which one processor is configured by a combination of one or more CPUs and software, and the processor functions as a plurality of processing units. Second, as represented by a system on chip (SoC) or the like, there is a form in which a processor is used in which the functions of the entire system which includes a plurality of processing units are realized by a single integrated circuit (IC) chip. As described above, the various processing units are configured by one or more various processors as a hardware structure.

Furthermore, the hardware structures of these various processors are, more specifically, an electric circuit (circuitry) in which circuit elements such as semiconductor elements are combined.

The technical scope of the present invention is not limited to the scope of the embodiments described above. The configurations and the like in the embodiments can be appropriately combined between the respective embodiments without departing from the spirit of the present invention.

EXPLANATION OF REFERENCES

10: medical image learning device
12: communicating unit
14: image database
16: operating unit
18: CPU
20: RAM
22: ROM
24: display unit
30: input unit
32: low resolution converting unit
34: interpolating unit
36: high-frequency component extracting unit
40: learning unit
42: generating unit
44: identification unit
46: addition unit
CR: original high-frequency component image
CV: virtual high-frequency component image
D1: meta information
G1, G2, G3, G4: CT image
G11, G12, G13: slice image
G21, G22, G23: slice image
G31, G32, G33: slice image
G41, G42, G43: slice image
GL1, GL2: low resolution image
GR: original high resolution image
GV: virtual high resolution image
S1 to S7: step of learning method of medical image

What is claimed is:

1. A learning method of a generative model that estimates, from a first image including low resolution information having a relatively low resolution, a second image including high resolution information having a relatively high resolution, the method comprising:
a first image generation step of generating the first image from a second image for learning;
a generator input step of inputting only the first image to a generator of a generative adversarial network including the generator which is a generative model that generates a virtual second image by using the first image and a discriminator that identifies the second image for learning and the virtual second image;
a first discriminator input step of inputting the second image for learning and meta information of the second image for learning to the discriminator, wherein the meta information comprises part information of the second image for learning, and wherein the part information of the second image comprises a plurality of different parts of an object; and
a second discriminator input step of inputting the virtual second image and meta information of the virtual second image to the discriminator, wherein the meta information of the virtual second image is the same as the meta information of the second image; and
a learning step of using the first image and the meta information to identify whether an input high resolution image is the second image or the virtual second image.

2. The learning method according to claim 1, wherein the part information includes a head, a chest, an abdomen, and a leg part of a human body.

3. The learning method according to claim 1, wherein the first image is a three-dimensional tomographic image, and the resolution is a resolution in a slice thickness direction.

4. The learning method according to claim 3, wherein in the first discriminator input step and the second discriminator input step, slice information of the first image is input to the discriminator.

5. The learning method according to claim 4, wherein the slice information is a slice interval.

6. The learning method according to claim 4, wherein the slice information is a slice thickness.

7. The learning method according to claim 1, wherein in the first discriminator input step and the second discriminator input step, the first image is input to the discriminator.

8. The learning method according to claim 1, further comprising a first image generation step of generating the first image from the second image for learning, wherein in the generator input step, only the generated first image is input to the generator.

9. The learning method according to claim 1, wherein the part information comprises a plurality of different parts of a human body.

10. A non-temporary computer-readable recording medium that causes a computer to execute the learning method according to claim 1 in a case in which a command stored in the recording medium is read by the computer.

11. A generative model that estimates, from a first image including low resolution information having a relatively low resolution, a second image including high resolution information having a relatively high resolution, the generative model being learned by the learning method according to claim 1.

12. A learning device of a generative model that estimates, from a first image including low resolution information having a relatively low resolution, a second image including high resolution information having a relatively high resolution, the device comprising:
a processor, configured to:
generate the first image from a second image for learning;
input only the first image to a generator of a generative adversarial network that includes a generator which is a generative model that generates a virtual second image by using the first image and a discriminator that identifies the second image for learning and the virtual second image;
input the second image for learning and meta information of the second image for learning to the discriminator, wherein the meta information comprises part information of the second image for learning, and wherein the part information of the second image comprises a plurality of different parts of an object; and
input the virtual second image and meta information of the virtual second image to the discriminator, wherein the meta information of the virtual second image is the same as the meta information of the second image; and
use the first image and the meta information to identify whether an input high resolution image is the second image or the virtual second image.

* * * * *